United States Patent
Bandyopadhyay et al.

(10) Patent No.: US 6,297,393 B1
(45) Date of Patent: Oct. 2, 2001

(54) PROCESS FOR THE PREPARATION OF MALONONITRILE

(75) Inventors: Ananda Kumar Bandyopadhyay; Khathija Aziz; Pravin Raybaji Likhar; Boyapati Manoranjan Choudary, all of Hyderabad (IN)

(73) Assignee: Council of Scientific and Industrial Research, New Dehli (IN)

( * ) Notice: Subject to any disclaimer, the term of this patent is extended or adjusted under 35 U.S.C. 154(b) by 0 days.

(21) Appl. No.: 09/652,378

(22) Filed: Aug. 31, 2000

(51) Int. Cl.⁷ .................................................. C07C 253/00

(52) U.S. Cl. .............................................................. 558/313

(58) Field of Search ................................................ 558/313

(56) References Cited

U.S. PATENT DOCUMENTS

| 2,389,217 | 11/1945 | Surrey | 260/464 |
| 2,799,697 | 7/1957 | Maxion | 260/465.2 |
| 3,317,587 | 5/1967 | Herschmann | 260/465.2 |
| 3,459,783 | 8/1969 | Budnick | 260/465.2 |

*Primary Examiner*—Joseph K. McKane
*Assistant Examiner*—Joseph Murray
(74) *Attorney, Agent, or Firm*—Ladas & Parry

(57) ABSTRACT

The invention describes an improved process for the preparation of malononitrile by using a porous particulate solid substance as efficient absorbent. Cyanoacetamide is reacted with $POCl_3$ as a dehydrating agent in a suitable solvent in the presence of an organic N-donor base as catalyst and a porous particulate solid substance as efficient absorbent. The product is then distilled under vacuum from the crude in the presence of a stabilizer into a receiver containing the same stabilizer, to obtain malononitrile of high purity and shelf-life.

8 Claims, No Drawings

PROCESS FOR THE PREPARATION OF MALONONITRILE

FIELD OF THE INVENTION

The present invention relates to an improved process for the preparation of malononitrile from cyanoacetamide. This invention particularly relates to an eco-friendly process for the synthesis of malononitrile from cyanoacetamide by using $POCl_3$ as the dehydrating agent, pyridine or an organic amine as catalyst and dispensing the use of solid absorbent, which replaces inorganic salt, to reduce polymerisation of meta-phosphoric acid by-product.

BACKGROUND OF THE INVENTION

Malononitrile is a versatile intermediate used extensively in synthetic organic chemistry. In industry, it is largely used as building block for a variety of pharmaceuticals and pesticides, such as thiamine (vitamin $B_1$), adenine, minoxidil (anti-hypertensive, Upjohn), thiopurinol (gout remedy), diuretic triamterene (Smith Kline), aminopeterin, bensulfuron-methyl (herbicide, Du Pont), etc. A variety of important methine dyes, in particular, aminoaryl cyanine based polyester dyes, characterized by high light fastness, are derived from malononitrile. Several important dyes belonging to this class are produced by major dye manufacturers such as Bayer, BASF, Ciba-Geigy, and Kodak. Malononitrile is also used in making tetracyanoquinodimethane (TCNQ), which forms with tetrathiafulvalene charge-transfer complex suitable for the production of conducting films in photocopiers and three-dimensional memories. On the other hand, o-chlorobenzylidene malononitrile (CS gas) is well-known tear gas with high safety factor.

Extensive literature search reveals that the preparation of malononitrile has largely relied upon dehydration of cyanoacetamide in a batch process utilizing a variety of dehydrating agents. It is also obtained in a continuous process involving gas phase reaction of cyanogen chloride and acetonitrile over a suitable catalyst at high temperature in a tube reactor.

Reference may be made to patents, such as U.S. Pat. No. 4,136,108, 1979; Neth. Appl. 80,04516, 1980; Swiss Appl. 68/6944, 1968; Ger. Often 3,006,492, 1981 wherein high conversion is attained in the transformation of acetonitrile to malonotirile. The drawbacks in the above described processes are the requirement of high reaction temperatures and low selectivity due to formation of maleic, succinic and fumeric acid by-products, which require efficient separation to obtain malononitrile in 60% yield (based on CNCl or MeCN).

Reference may be made to the patent U.S. Pat. No. 5,959,136, 1999 wherein malononitrile is made from an isonitrile, optionally in the presence of a nitrile by using a similar procedure. The drawback in the above process is the requirement of high temperature for the activation of isonitrile, which isomerizes to nitrile, the reactive ingredient in the previous process.

Reference may be made to publication by E. M. Gal and A. T. Shulgin J. Amer. Chem. Soc. 73, 2938, 1951 wherein $P_2O_5$ is employed as dehydrating agent. The drawback in the above described process is that the dehydrating agent is less effective in terms of selectivity and yield as compared to $POCl_3$.

Reference may be made to publications by B. B. Corson, R. W. Scott and C. E. Vose Org. Synth. 10, 66, 1930; A. J. Fatidadi Synthesis 165, 1978 and patents, such as U.S. Pat No. 2,802,857, 1957; Brit. 1,163,397, 1969, wherein $PCl_5$ is employed as dehydrating agents. The drawback in the above described process is that the dehydrating agent is less effective in terms of selectivity and yield as compared to $POCl_3$.

Reference may be made to publications by Surrey, Org. Synth. 25, 63, 1945; J. Amer. Chem. Soc 65, 2471, 1943 wherein the preparation of malononitrile by elimination of water from cyanoacetamide, is extensively studied by employing $POCl_3$ as dehydrating agent.

In $POCl_3$ based procedures, a suspension of cyanoacetamide in dichloroethane is refluxed in the presence of $POCl_3$. Nevertheless, this dehydration protocol possesses a severe process limitation when applied to large-scale synthesis due to formation of metastable phosphoric acid as side product, which, under the reaction conditions, tends to form hard polymeric crust along the reactor wall inhibiting uniform stirring and heating.

Moreover, a considerable portion of suspended starting material remains embedded within the coating causing substantial lowering of the yield. In order to avoid polymerisation of meta-phosphoric acid, inorganic salts are employed to convert it into its salt, which is precipitated from the reaction mixture. Several processes, employing alkali metal salts and alkaline earth metal salts, are disclosed.

Reference may be made to patents, for example, U.S. Pat. No. 2,389,217, 1945 and U.S. Pat. No. 2,799,697, 1957 wherein alkali metal salts are used for the purpose. The drawback in the above described process is that they involve consumption of a large quantity of inorganic salt, which is required in stoichiometric amount and can not be easily recovered due to the presence of tarry polymeric products. Thus, in the patent U.S. Pat. No. 2,389,217, 1945 1.00 Kg NaCl per 1.26 Kg cyanoacetamide is recommended and no salt recovery is prescribed.

Reference may be made to publication by R. Malinowski and J. Legocki Organika 53, 1977 and U.S. Pat. No. 3,459, 783, 1969 wherein alkaline earth metal salts are used. The drawback in the above described processes is that they involve consumption of a large quantity of inorganic salt, which is required in stoichiometric amount and can not be easily recovered due to the presence of tarry polymeric products.

However, in synthesizing malononitrile by utilizing above procedure, only a marginal improvement is noted since the formation of the polymeric product cannot be completely prevented. Therefore, notwithstanding the foregoing, the art has not heretofore taught or suggested a methodology that ensured process compatibility as well as offered environmentally clean technology.

OBJECT OF THE INVENTION

The principal objective of the present invention is to provide an alternate, efficient technology for the synthesis of malononitrile from the reaction of cyanoacetamide and $POCl_3$ in a batch process, which obviates the drawbacks as detailed above.

Another objective of the present invention is to disclose a strategy in which a smooth process operation is secured by replacing inorganic salt with porous solid material to eliminate formation of polymeric by-product in the reaction medium.

Still another objective of the present invention is to develop an eco-friendly process by avoiding the use of large quantities of inorganic salts, which require proper disposal.

Still another objective of the present invention is to provide an improved method for the isolation of pure malononitrile from crude product by recommending the use of appropriate stabilizer during vacuum distillation.

Still another objective of the present invention is to provide a method for storage of isolated malononitrile by prescribing the use of a suitable stabilizer so that a prolonged shelf-life is achieved.

SUMMARY OF THE INVENTION

Accordingly, the present invention describes an improved process for the preparation of malononitrile characterised in using a porous particulate solid substance as efficient absorbent, wherein the said process comprises reacting cyanoacetamide with $POCl_3$ as a dehydrating agent in a suitable solvent in the presence of an organic N-donor base as catalyst and a porous particulate solid substance as efficient absorbent at a temperature in the range 80–120° C. for 6–8 hours and distilling the product under vacuum from the crude in the presence of a stabilizer into a receiver containing the same stabilizer, to obtain the desired product of high purity and shelf-life.

In one embodiment of the present invention, the solid absorbent used may be silica gel of 60–120 mesh size employed in 38–70 parts per 250 parts of cyanoacetamide.

In another embodiment of the present invention the N-donor organic base catalyst is preferably selected from pyridine or sec- or tert-amine present in an optimal concentration ranging between 2.3–3.0 mol% with respect to the substrate.

In still another embodiment of the present invention the solvent used may be selected from the group consisting of toluene, dichloroethane (DCE), chlorobenzene, and o-dichlorobenzene.

In yet another embodiment of the present invention the solvent used may be recovered from the reaction mixture by rotavapor and may be re-used in the process without further purification and treatment.

In yet another embodiment of the present invention the temperature of the reaction is preferably in the range of 80–120° C.

In still another embodiment of the present invention the stabilizer, used to reduce thermal degradation of malononitrile during vacuum distillation, is preferably selected from the group comprising of butylated hydroxytoluene (BHT), hydroquinone (HQ), tris (nonylphenyl) phosphite (TNPP) and tris (2,4-di tert-butyl) phosphite (TBPP).

In a further embodiment of the invention, the crude product is distilled out at about 90° C. and 2.0 mm pressure in the presence of 0.1–0.5 weight % of the stabilizer to obtain an improved isolated yield (96–98%).

In still another embodiment of the present invention the stabilizer used may be employed in the range of 0.05–0.15 weight % concentration to effect prolonged storage of malononitrile thereby imparting to it enhanced shelf-life.

The novelty of the present invention lies in the use of a porous particulate solid substance, abundantly available commercially, such as silica gel 60–120 mesh size, as efficient absorbent of phosphoric acid-derived polymeric by-product formed in the synthesis of malononitrile from the known reaction of cyanoacetamide with $POCl_3$ in toluene or halocarbon solvent in the presence of organic N-donor base as catalyst and a porous particulate solid substance as efficient absorbent at a temperature in the range 80–120° C. for 6–8 hours. This invention offers excellent yields and ensures smooth process operation, greater selectivity towards malononitrile and reduced waste. Application of a suitable stabilizer during both isolation of the product by distillation of the crude under vacuum as well as during storage of the product results in enhanced isolated yield and improved storage. These advantages are quite obvious, when compared with the processes currently practiced utilizing stoichiometric amount of inorganic salt, which generates large volumes of solid wastes. Therefore, the process described in this invention is technically feasible, economically viable and environmentally friendly.

DETAILED DESCRIPTION OF THE INVENTION

The present invention describes an improved process which comprises a novel approach to the desired synthesis of malononitrile from the known reaction of cyanoacetamide with $POCl_3$ in suitable solvent in the presence of organic N-donor organic base as catalyst and a porous particulate solid substance as efficient absorbent at a temperature in the range 80–120° C. for 6–8 hours and distilling the product under vacuum from the crude containing a stabilizer into a receiver containing the same stabilizer, so that product of high purity and high shelf-life is obtained.

The solid absorbent represents, for the first time, silica gel 60–120 mesh size, which is employed in 38–70 parts per 250 parts of cyanoacetamide. The N-donor organic base catalyst may be such as pyridine or sec- or tert-amine, present in an optimal concentration such as 2.3–3.0 mol% with respect to the substrate. The solvent used may be selected from toluene, dichloroethane (DCE), chlorobenzene, and o-dichlorobenzene, etc. The solvent used in the process of the invention is capable of being recovered from the reaction mixture by rotavapor and may be re-used in the process without further purification and treatment. The temperature of the reaction may be preferably in the range of 80–120° C.

The stabilizer, used to reduce thermal degradation of malononitrile during vacuum distillation, is generally selected from the group consisting of butylated hydroxytoluene (BHT), hydroquinone (HQ), tris (nonylphenyl) phosphite (TNPP) and tris (2,4-di tertbutyl) phosphite (TBPP). The crude product is distilled out at 90° C. and 2.0 mm pressure in the presence of 0.1–0.5 weight % of the stabilizer to obtain an improved isolated yield (96–98%). The stabilizer used may be employed in the range of 0.05–0.15 weight % concentration to effect prolonged storage of malononitrile thereby imparting to it enhanced shelf-life.

SCIENTIFIC EXPLANATION

The efficacy of the processes for the preparation of malononitrile by dehydration of cyanoacetamide could not be fully exploited for large-scale synthesis in the prior art processes, due the problems associated with the presence of large quantities of hard polymeric materials. For the invention, it was decided to test a highly porous solid active absorbent, preferably in fine particulate form since this might effectively prevent the formation of rigid polymeric coating, which causes difficulties during the process operation, as enumerated above. This strategy relies on appropriate choice of solid absorbent in fine particulate form, which allows deposition on its surface of the polymeric substance formed during the reaction. In the present invention, silica gel of 60–120 mesh size, which is abundantly available commercially at affordable price, is used as the solid absorbent.

Without being bound by any theory, it is believed that the key success to the present invention is attributable to the fact that the amount of silica gel required to achieve complete dispersion of the phosphoric acid-derived polymers, is well below the stoichiometric level. This reduces the disposal of rather large quantity of inorganic salts, which were being used in stoichiometric amount in earlier processes for the same purpose.

Furthermore, the present invention ascertains the optimum concentration of pyridine, which is required to achieve maximum conversion of cyanoacetamide with the highest selectivity for malononitrile. The synthesis of malononitrile, carried out in our laboratory following the procedure detailed in earlier patent (Lonza Ltd., Fr. 1,365,202, 1964) and using the prescribed quantity of pyridine (1 mol %), resulted in considerably slow reaction. On the contrary, high concentration of pyridine base resulted in faster reaction but favoured polymerisation of malononitrile [A. J. Fatiadi, Synthesis 165, 1978] and consequently low selectivity. The present invention shows that the highest selectivity of the desired product is obtained when pyridine catalyst is employed in 2.3–2.5 mol % with respect to the substrate. It was also observed that the solvent recovered from the reaction mixture under reduced pressure of rotavapor is capable of re-use without further purification.

The product malononitrile is stabilised against thermal degradation by employing butylated hydroxytoluene (BHT) as the stabilizing agent, polymerisation/decomposition of the crude product during vacuum distillation is considerably reduced leading to higher isolated yield. Thus, in the presence of BHT (0.10 weight %) about 97% mass is distilled out from the crude product at 90° C. and 2 mm pressure. Moreover, in the presence of BHT (0.05 weight %) improved shelf-life of malononitrile is obtained. Thus, the invented strategy offers an environmentally acceptable and extremely convenient catalytic process for the synthesis of malononitrile from the reaction of cyanoacetamide and $POCl_3$ in batch process.

The following examples are given by way of illustration of the present invention and therefore should not be construed to limit the scope of the present invention.

EXAMPLE 1

Reagents used are purified as follows: DCE, pyridine and $POCl_3$ are freshly distilled, the former two after being dried by using appropriate drying agents. Cyanoacetamide and silica gel used in the process are dried in oven at 80° C. for overnight.

A three litre two-necked round bottom flask, equipped with a reflux condenser and mechanical stirrer and flashed with nitrogen, is charged with cyanoacetamide (250 g, 2.98 moles), $POCl_3$ (252.6 g, 1.65 moles) 60–120 mesh silica gel (70 g), pyridine (5.47 g, 0.069 moles) and DCE (787 mL). The open end of the water-cooled condenser is connected to a water scrubber to trap HCl generated during the reaction. The reaction mixture is heated slowly to 900° C. under continuous stirring. After two hours the stirring speed is increased to about 500 rpm to avoid agglomeration of the suspended solid, which at this point loses its free-flowing property. The progress of the reaction is monitored by TLC. After stirring for 8h under reflux condition the reaction mixture is cooled to room temperature, filtered through Buchner funnel and washed with 2×100 mL DCE. Complete removal of the solvent and volatile under reduced pressure followed by distillation of the orange residual liquid in presence of 150 mg butylated hydroxytoluene (BHT) under vacuum afforded malononitrile (149 g, 76% yield) in 99.92% purity.

EXAMPLE 2

Following the standard procedure as above and utilizing the following amounts of reagents: cyanoacetamide 9250 g, 2.98 moles), $POCl_3$ (252.6 g, 1.65 moles) 60–120 mesh silica gel (38 g), pyridine (5.47 g, 0.069 moles) and DCE (787 mL), refluxing for 8h, removal of the solvent followed by vacuum distillation as described above afforded pure (>99.9%) malononitrile (145 g, 74% yield).

EXAMPLE 3

The solvent DCE, recovered from the first experiment (Example 1), is used here without further purification. All other regents are purified as described earlier.

Following the standard procedure as above and utilizing the following amounts of reagents: cyanoacetamide (100 g, 1.19 moles) $POCl_3$ (101 g, 0.66 moles), 60–120 mesh silica gel (28 g), pyridine (2.19 g, 0.028 moles) and DCE (314 mL), refluxing for 6h afforded crude product (49 g, 88% yield). Vacuum distillation of the crude product in the presence of 50 mg of BHT resulted in isolation of pure (>99.9%) malononitrile (59 g, 75% yield).

EXAMPLE 4

The solvent DCE, recovered from the first experiment (Example 1), is used here without further purification. All other reagents are purified as described earlier.

Following the standard procedure as in Example 1 and utilizing the following amounts of reagents: cyanoacetamide (100 g, 1.19 moles), $POCl_3$ (101 g, 0.66 moles), 60–120 mesh silica gel (28 g), pyridine (2.19 g, 0.028 moles) and DCE (314 mL), refluxing for 6h afforded crude malononitrile product (49 g, 88% yield). In contrast to the earlier examples, vacuum distillation of the crude product in the absence BHT afforded 66% yield malononitrile in 99.90% purity.

EXAMPLE 5

Storage of malononitrile: Freshly distilled malononitrile (100 g, 99.92% purity by GC) is collected in a receiving flask containing 50 mg butylated hydroxytoluene (BHT). The mixture is thoroughly mixed and transferred into an air-filled, coloured and tightly capped bottle and stored at room temperature (35–38° C.) in the air for 6 weeks. The compound remained as a clear transparent colourless liquid and no visible change occurred during the period. The purity at the end of the sixth week is 99.8% as determined by GC.

The Main Advantages of the Present Invention Are:

1. The present invention comprises a novel approach to the desired synthesis of malononitrile from the reaction of cyanoacetamide in excellent yield without any operational difficulty experienced during the course of the reaction.
2. The solid porous material used for absorbing the polymeric by-product is cheap and abundantly available commercially.
3. The present process envisages optimal use of pyridine or an organic amine as catalyst to ensure highest product selectivity.
4. An eco-friendly and very simple synthetic protocol is developed. Problem associated with disposal of inorganic salt does not arise.
5. The selectivity, yield and purity of malononitrile produced in this process are quite high.
6. The reaction conditions are relatively mild.

7. Monitoring of the reaction and subsequent work-up procedures are easy.
8. Isolation of the product from the crude reaction mixture is straightforward due to negligible formation of organic by-products, which are considered less volatile.
9. The present process describes a simple protocol for reducing the degradation of thermally sensitive product malononitrile that, in turn, contributes to higher isolated yield.
10. The present process discloses simple means of storage of malonoitrile thereby achieving higher shelf-life.
11. The overall process is economical.

We claim:

1. A process for the preparation of malononitrile characterised in using a porous particulate solid substance as efficient absorbent, wherein the said process comprises reacting cyanoacetamide with $POCl_3$ as a dehydrating agent in a solvent in the presence of an organic N-donor base as catalyst and a porous particulate solid substance as efficient absorbent at a temperature in the range of 80–120° C. for 6–8 hours and distilling the product under vacuum from the crude in the presence of stabiliser into a receiver containing the same stabilizer, to obtain the desired product of high purity and shelf life.

2. A process as claimed in claim 1, wherein the solid absorbent used is silica gel of 60–120 mesh size and is employed in 38–70 parts per 250 parts of cyanoacetamide.

3. A process as claimed in claim 1, wherein the N-donor organic base catalyst used is selected from pyridine and sec- or tert-amine present in optimal concentration ranging between 2.3–3.0 mol % with respect to the substrate.

4. A process as claimed in claim 1, wherein, the solvent used is selected from the group consisting of toluene, dichloroethane (DCE), chlorobenzene, o-dichlorobenzene.

5. A process as claimed in claim 4, where the solvent used is recovered from the reaction mixture of a previous experiment by rotavapor, are re-used in the process without further purification and treatment.

6. A process as claimed in claim 1 wherein, the stabilizer used to reduce thermal degradation of malononitrile during vacuum distillation, is selected from the group consisting of butylated hydroxytoluene (BHT), hydroquinone (HQ), tris(nonylphenyl)-phosphite (TNPP), tris(2,4-di-tert-butyl) phosphite (TBPP).

7. A process as claimed in claim 1 wherein crude product is distilled out at about 90° C. and 2.0 mm pressure in the presence of 0.1–0.5 weight % of the stabilizer to obtain an improved isolated yield (97%).

8. A process as claimed in claim 1, wherein the stabilizer used is employed in the range of 0.05–0.15 weight % concentration to effect prolonged storage of malononitrile thereby imparting to it enhanced shelf-life.

* * * * *